United States Patent [19]

Farooq

[11] Patent Number: 4,874,778
[45] Date of Patent: Oct. 17, 1989

[54] 1-CARBAMOYL-2-PYRAZOLINES, COMPOSITION CONTAINING THEM, AND INSECTICIDAL AND ACARICIDAL METHOD OF USING THEM

[75] Inventor: Saleem Farooq, Arisdorf, Switzerland

[73] Assignee: Ciba-Geigy Corporation, Ardsley, N.Y.

[21] Appl. No.: 65,667

[22] Filed: Jun. 22, 1987

Related U.S. Application Data

[63] Continuation of Ser. No. 796,379, Nov. 8, 1985, abandoned.

[30] Foreign Application Priority Data

Nov. 16, 1984 [CH]  Switzerland ................. 5489/84
Oct. 22, 1985 [CH]  Switzerland ................. 4551/85

[51] Int. Cl.$^4$ ................. A01N 43/56; C07D 231/06
[52] U.S. Cl. ................................. 514/403; 548/379
[58] Field of Search ..................... 548/379; 514/403

[56] References Cited

U.S. PATENT DOCUMENTS

| | | | |
|---|---|---|---|
| 4,174,393 | 11/1979 | Van Dahlen et al. | 548/379 |
| 4,439,440 | 3/1984 | Van Hes et al. | 548/379 |
| 4,540,706 | 9/1985 | Ozawa et al. | 548/379 |

FOREIGN PATENT DOCUMENTS

| | | | |
|---|---|---|---|
| 0004733 | 10/1979 | European Pat. Off. | 548/379 |
| 2529689 | 1/1976 | Fed. Rep. of Germany | 548/379 |
| 2700258 | 7/1977 | Fed. Rep. of Germany | 548/379 |

Primary Examiner—Robert W. Ramsuer
Assistant Examiner—Kurt G. Briscoe
Attorney, Agent, or Firm—Edward McC. Roberts

[57] ABSTRACT

The invention relates to 1-carbamoyl-3-phenyl-4-benzyl-$\Delta^2$-pyrazolines of the formula

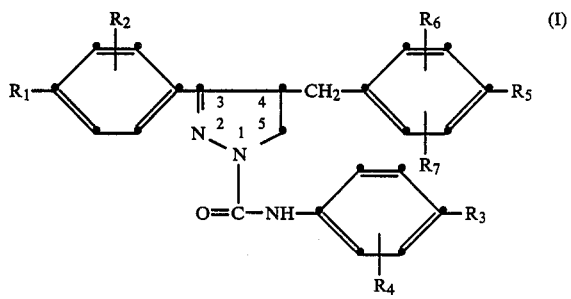

wherein
$R_1$ and $R_2$ are each independently hydrogen, methyl halogen, trifluoromethyl, $C_1$–$C_4$haloalkoxy containing 1 to 7 halogen atoms or $C_1$–$C_4$haloalkylthio containing 1 to 7 halogen atoms;
$R_3$ is hydrogen, halogen, $C_1$–$C_4$alkyl, $C_1$–$C_4$haloalkyl containing 1 to 7 halogen atoms, $C_1$–$C_4$alkoxy, $C_1$–$C_4$haloalkoxy containing 1 to 7 halogen atoms or alkoxycarbonyl containing 1 to 4 carbon atoms in the alkyl moiety;
$R_4$ is hydrogen, halogen, $C_1$–$C_4$alkyl or trifluoromethyl;
$R_5$ is hydrogen, halogen, $C_1$–$C_4$alkyl, trifluoromethyl or $C_1$–$C_4$alkoxy; and
$R_6$ and $R_7$ are each independently hydrogen, halogen or trifluoromethyl or $R_6$ and $R_5$ or $R_7$ and $R_5$ are methylenedioxy;

to the preparation of these compounds and to compositions containing them for controlling insects and representatives of the order Acarina, especially plant-destructive feeding insects and soil insects.

8 Claims, No Drawings

1-CARBAMOYL-2-PYRAZOLINES, COMPOSITION CONTAINING THEM, AND INSECTICIDAL AND ACARICIDAL METHOD OF USING THEM

This application is a continuation of application Ser. No. 796,379, filed 11/8/85, now abandoned.

The present invention relates to 1-carbamoyl-3-phenyl-4-benzyl-$\Delta^2$-pyrazolines, to the preparation thereof and to the use thereof in pest control.

The compounds of this invention are of formula I

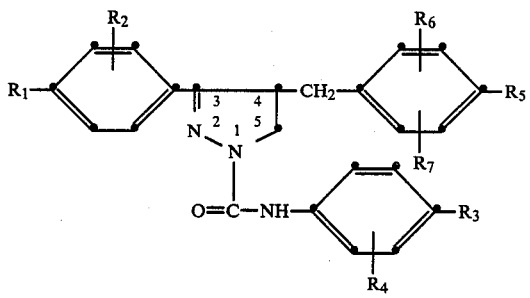

wherein $R_1$ and $R_2$ are each independently hydrogen, methyl halogen, trifluoromethyl, $C_1$-$C_4$haloalkoxy containing 1 to 7 halogen atoms or $C_1$-$C_4$haloalkylthio containing 1 to 7 halogen atoms;

$R_3$ is hydrogen, halogen, $C_1$-$C_4$alkyl, $C_1$-$C_4$haloalkyl containing 1 to 7 halogen atoms, $C_1$-$C_4$alkoxy, $C_1$-$C_4$haloalkoxy containing 1 to 7 halogen atoms or alkoxycarbonyl containing 1 to 4 carbon atoms in the alkyl moiety;

$R_4$ is hydrogen, halogen, $C_1$-$C_4$alkyl or trifluoromethyl;

$R_5$ is hydrogen, halogen, $C_1$-$C_4$alkyl, trifluoromethyl or $C_1$-$C_4$alkoxy; and $R_6$ and $R_7$ are each independently hydrogen, halogen or trifluoromethyl or $R_6$ and $R_5$ or $R_7$ and $R_5$ are methylenedioxy.

To be singled out for particular mention are those compounds of formula I, wherein $R_2$, $R_4$, $R_6$ and $R_7$ are hydrogen.

Preferred compounds of formula I are those wherein $R_1$ is hydrogen, fluorine, chlorine or $C_1$-$C_3$haloalkoxy containing 1 to 7 fluorine or chlorine atoms;

$R_2$ is hydrogen;

$R_3$ is hydrogen, fluorine, chlorine, $C_1$-$C_3$alkoxy, $C_1$-$C_3$haloalkoxy containing 1 to 7 fluorine, chlorine or bromine atoms or isopropoxycarbonyl;

$R_4$ is hydrogen, methyl or ethyl;

$R_5$ is hydrogen, fluorine, chlorine, bromine, $C_1$-$C_3$alkyl, trifluoromethyl or $C_1$-$C_3$alkoxy;

$R_6$ is hydrogen, fluorine in the 2- or 3-position or chlorine in the 2- or 3-position or $R_6$ and $R_5$ are a 3,4-methylenedioxy group; and $R_7$ is hydrogen or 6-chlorine.

Further preferred compounds of formula I are those wherein $R_1$ is hydrogen, fluorine, chlorine or methyl;

$R_2$ is hydrogen;

$R_3$ is fluorine, chlorine or trifluoromethoxy, difluorobromomethoxy or isopropoxycarbonyl;

$R_4$ is hydrogen or 3-methyl;

$R_5$ is hydrogen, fluorine, chlorine, bromine or methyl;

$R_6$ is hydrogen or 3-chlorine; and $R_7$ is hydrogen;

as well as those of formula I, wherein $R_1$ is hydrogen, fluorine or chlorine;

$R_2$, $R_4$, $R_6$ and $R_7$ are hydrogen;

$R_3$ is chlorine or trifluoromethoxy; and $R_5$ is fluorine or chlorine.

Depending on the number of carbon atoms indicated, within the scope of the present invention alkyl by itself or as moiety of another substituent will be understood as meaning straight chain or branched alkyl radicals, for example the following groups: methyl, ethyl, propyl, butyl, and the isomers thereof, e.g. isopropyl, isobutyl, tert-butyl, sec-butyl.

Haloalkyl within the scope of the present invention will be understood as meaning alkyl radicals such as methyl, ethyl, n-propyl, isopropyl and butyl etc., which are substituted by 1 to 7 different or identical halogen atoms. Said alkyl radicals may be perhalogenated alkyl radicals or alkyl radicals in which the hydrogen atoms are only partially substituted by halogen.

Halogen within the scope of the present invention will be understood as meaning fluorine, chlorine and bromine, with fluorine and chlorine being preferred.

The compounds of formula I can be prepared by processes analogous to known ones (q.v. e.g. German Offenlegungsschrift specifications Nos. 2 529 689 and 2 700 258 and European patent application No. 0 004 733).

Thus, for example, a compound of formula I can be obtained by reacting a compound of formula II

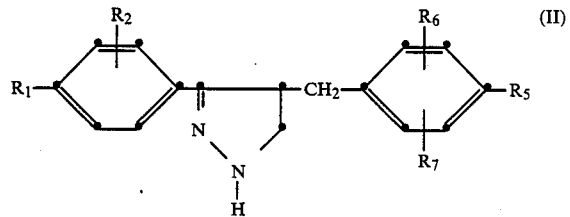

with a compound of formula III

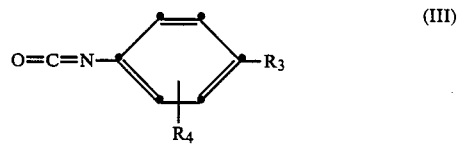

in which formulae II and III the radicals $R_1$ to $R_7$ are as defined above for formula I.

The above process can preferably be carried out under normal pressure and in the presence of an organic solvent or diluent which is inert to the reactants. Suitable solvents or diluents are e.g. ethers and ethereal compounds such as diethyl ether, dipropyl ether, dibutyl ether, dioxane, dimethoxyethane and tetrahydrofuran; N,N-dialkylated carboxamides; aliphatic, aromatic and halogenated hydrocarbons, especially benzene, toluene, xylene, chloroform, methylene chloride, carbon tetrachloride and chlorobenzen; nitriles such as acetonitrile or propionitrile; dimethyl sulfoxide; and ketones such as acetone, methyl ethyl ketone, methyl ispropyl ketone and methyl isobutyl ketone. In general, the process can be carried out readily in the temperature range from −10° to 100° C., preferably from 10° to 30° C., e.g. at room temperature, optionally in the presence of a suitable aprotic, organic base, e.g. triethylamine, N-methylmorpholine or pyridine.

The starting materials of formulae II and III are known and can be prepared by processes analogous to known ones. The 3-phenyl-4-benzyl-$\Delta^2$-pyrazolines of formula II can be obtained e.g. by reacting a corresponding β-phenylpropiophenone of formula IV

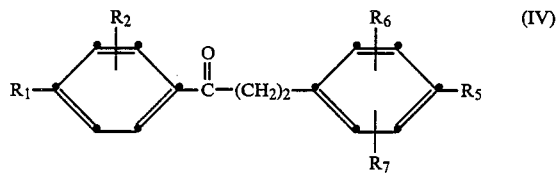

with formaldehyde, at elevated temperature and in the presence of a catalyst, and cyclising the resultant 1-phenyl-2-benzyl-prop-2-en-1-one of formula V

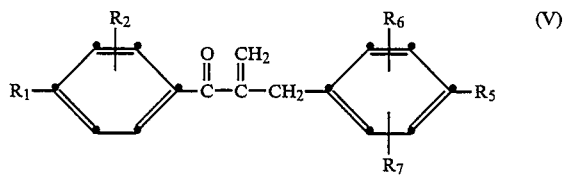

by condensation with hydrazine (q.v. the above references to the literature).

The propiophenone of formula IV is obtainable by hydrogenating a corresponding benzylideneacetophenone of formula VI

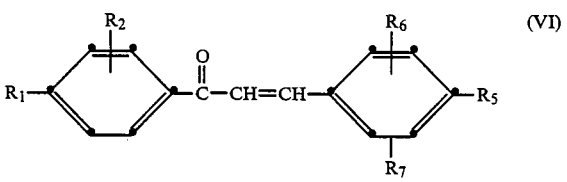

by a conventional method. In the above formulae IV to VI $R_1$, $R_2$, $R_5$, $R_6$ and $R_7$ are as defined for formula I.

Substituted 1-carbamoyl-3-phenyl-$\Delta^2$-pyrazolines having insecticidal properties are known from German Offenlegungsschrift specifications Nos. 2 529 689 and 2 700 258 and European patent application No. 0 004 733. Compared with these known compounds, the compounds of formula I of the present invention differ structurally in particular by the presence of a benzyl group in place of a phenyl radical in the 4-position of the $\Delta^2$-pyrazoline ring.

Surprisingly, it has been found that the compounds of formula I of the present invention have excellent properties as pesticides while being well tolerated by plants and having low toxicity to warm-blooded animals. They are particularly suitable for controlling insects and representatives of the order Acarina that attack plants and animals.

In particular, the compounds of formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina of the families: Ixodidae, Argasidae, Tetranychidae and Dermanyssidae.

In addition to their action against flies, e.g. *Musca domestica*, and mosquito larvae, the compounds of formula I can also be used for controlling plant-destructive feeding insects in ornamentals and crops of useful plants, especially in cotton (e.g. against *Spodoptera littoralis* and *Heliothis virescens*) and in crops of fruit and vegetables (e.g. *Laspeyresia pomonella*, *Leptinotarsa decemlineata* and *Epilachna varivestis*). The compounds of formula I have a pronounced larvicidal action against insects, in particular against larvae and nymphs of noxious feeding insects. If compounds of formula I are ingested by adult insect stages with the feed, then a diminished oviposition and/or reduced hatching rate is observed in many insects, in particular in Coleoptera, e.g. *Anthonomus grandis*. The compounds of this invention are also suitable for controlling soil insects (e.g. *Aulacophora femoralis*, *Chortophila brassicae*, *Diabrotica balteata*, *Pachnoda savigni* and *Scotia ypsilon*). The compounds of formula I can also be used with great success against plant-destructive cicadas, especially in crops of rice, and have both systemic and contact action.

The compounds of formula I can also be used for controlling ectoparasites such as *Lucilia sericata*, in domestic animals and producive livestock, e.g. by treating animals, cowsheds, barns, stables etc., and pastures.

The good pesticidal activity of the compounds of formula I of the invention corresponds to a mortality of at least 50–60% of the above pests.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and *Bacillus thuringiensis* preparations.

By the addition of compounds of formula I, the insecticidal activity of the known insecticide dimethyl-(Z)-1-methyl-2-methylcarbamoyl vinyl phosphate can be increased or activated.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mxing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are nonionic, cationic and/or anionic surfacants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g., polyoxyethylene sorbitan trioleate, are also suitable non-ionic surfactants.

Cationic sufactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates, or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hanser Verlag, Munich/Vienna, 1981.

The pesticidal compositions of this invention usually contain 0.1 to 99%, preferably 0.1 to 95%, of a compound of formula I or combination thereof with other insecticides, or acaricides, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration.

The compositions may also contain further ingredients, such as stabilisers, antifoams, viscosity regulators, binders, tackifiers as well as fertilisers or other active ingredients in order to obtain special effects.

EXAMPLE 1

(a) Preparation of 4,4'-difluoro-β-phenylpropiophenone

A solution of 59.9 g of 4,4'-difluorobenzylideneacetophenone in 600 ml of tetrahydrofuran is hydrogenated in the presence of 6 g of Raney nickel. After removal of the catalyst, the reaction mixture is concentrated by rotary evaporation, affording the title compound of the formula

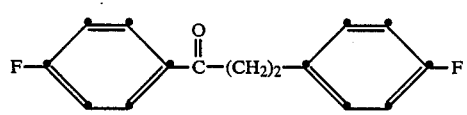

as a crude product with a refractive index of $n_{20}{}^D = 1.5478$.

(b) Preparation of 3-(4-fluorophenyl)-4-(4-fluorobenzyl)-$\Delta^2$-pyrazoline 59.4 g of 4,4'-difluoro-β-phenylpropiophenone, prepared in accordance with step (a), together with 39.2 g of dimethylamine hydrochloride and 14.4 g of paraformaldehyde are heated overnight under reflux. The reaction mixture is then concentrated by evaporation and the residue is taken up in 300 ml of water and is extracted with three 200 ml portions of ether. The combined ether extracts are washed twice with water and then twice with a saturated solution of NaCl, dried over Na₂SO₄ and filtered. The filtrate is concentrated, affording 1-(4-fluorophenyl)-2-(4-fluorobenzyl)-prop-2-en-1-one of the formula

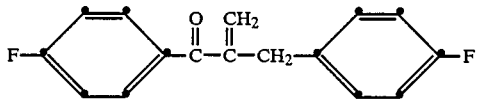

as a crude product which is immediately reacted further. The crude product is dissolved in 140 ml of ethanol and a solution of 18.8 g of hydrazine hydrate in 70 ml of methanol is added dropwise to this ethanolic solution. When the addition is complete, the reaction mixture is heated under reflux for three hours, cooled and then concentrated by rotary evaporation. The resultant residue is taken up in ether and the ethereal solution is washed twice with water and then twice with a saturated solution of NaCl, dried over Na₂SO₄ and filtered. The filtrate is concentrated by evaporation, thus affording the title compound of the formula

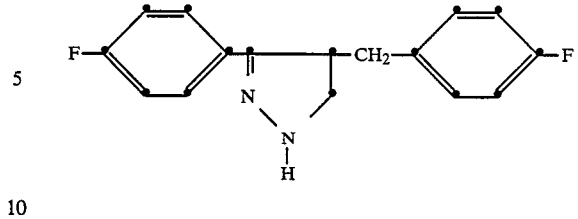

(c) Preparation of 1-(4-trifluoromethoxyphenylcarbamoyl)-3-(4-fluorophenyl)-4-(fluorobenzyl)-Δ²-pyrazoline A reaction vessel is charged with a solution of 20 g of 3-(4-fluorophenyl)-4-(4-fluorobenzyl)-Δ²-pyrazoline, prepared in accordance with step (b), in 50 ml of ether. With ice cooling, 14.9 of 4-trifluoromethoxyphenylisocyanate are added dropwise to this solution. After one hour at room temperature, the precipitated product is isolated by filtration, washed with ether and dried. The resultant title compound of the formula

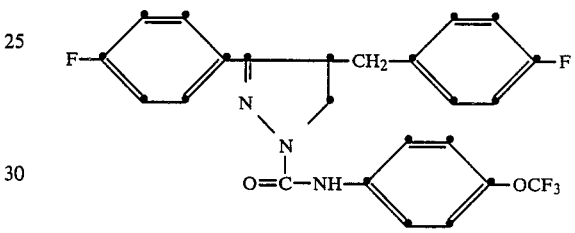

ps has a melting point of 98°–100° C. (compound 1).
The following compounds of formula I are prepared by procedures analogous to those described above.

| Compound | R₁ | R₂ | R₃ | R₄ | R₅ | R₆ | R₇ | Physical data |
|---|---|---|---|---|---|---|---|---|
| 2 | H | H | H | H | 3,4—O—CH₂—O— | | H | m.p. 107–109° C. |
| 3 | H | H | H | 3-CH₃ | 3,4—O—CH₂—O— | | H | m.p. 121–123° C. |
| 4 | H | H | —CO—O—CH(CH₃)₂ | H | 3,4—O—CH₂—O— | | H | viscous mass |
| 5 | H | H | H | H | Cl | H | H | m.p. 142–144° C. |
| 6 | H | H | H | 3-CH₃ | Cl | H | H | m.p. 134–135° C. |
| 7 | H | H | —O—CF₃ | H | Cl | H | H | m.p. 114–116° C. |
| 8 | H | H | —O—CBrF₂ | H | Cl | H | H | m.p. 109–111° C. |
| 9 | H | H | H | H | Br | H | H | m.p. 150–152° C. |
| 10 | H | H | H | 3-CH₃ | Br | H | H | m.p. 132–135° C. |
| 11 | H | H | —O—CF₃ | H | Br | H | H | m.p. 128–129° C. |
| 12 | H | H | H | H | F | H | H | m.p. 128–130° C. |
| 13 | H | H | —CO—O—CH(CH₃)₂ | H | Cl | H | H | m.p. 68–70° C. |
| 14 | H | H | H | 3-CH₃ | F | H | H | m.p. 129–131° C. |
| 15 | H | H | —O—CF₃ | H | F | H | H | m.p. 107–108° C. |
| 16 | H | H | H | H | —CH₃ | H | H | m.p. 128–130° C. |
| 17 | H | H | —CO—O—CH(CH₃)₂ | H | —CH₃ | H | H | m.p. 67–69° C. |
| 18 | H | H | H | 3-CH₃ | —CH₃ | H | H | m.p. 126–128° C. |
| 19 | H | H | —O—CF₃ | H | —CH₃ | H | H | m.p. 134–136° C. |
| 20 | H | H | H | H | Cl | 3-Cl | H | m.p. 129–131° C. |
| 21 | H | H | H | 3-CH₃ | Cl | 3-Cl | H | m.p. 134–136° C. |
| 22 | H | H | —O—CF₃ | H | Cl | 3-Cl | H | m.p. 118–120° C. |
| 23 | H | H | H | H | H | 6-Cl | 2-Cl | m.p. 188–190° C. |
| 24 | H | H | H | 3-CH₃ | H | 6-Cl | 2-Cl | m.p. 178–180° C. |
| 25 | H | H | —O—CF₃ | H | H | 6-Cl | 2-Cl | m.p. 180–182° C. |
| 26 | Cl | H | H | H | Cl | H | H | m.p. 133–135° C. |
| 27 | F | H | H | H | F | H | H | m.p. 124–126° C. |
| 28 | F | H | H | 3-CH₃ | F | H | H | m.p. 96–98° C. |
| 29 | —CH₃ | H | H | H | —CH₃ | H | H | m.p. 151–153° C. |
| 30 | —CH₃ | H | H | 3-CH₃ | —CH₃ | H | H | m.p. 130–132° C. |
| 31 | —CH₃ | H | —O—CF₃ | H | —CH₃ | H | H | m.p. 108–109° C. |
| 32 | —CH₃ | H | H | H | Cl | 3-Cl | H | m.p. 160–162° C. |
| 33 | —CH₃ | H | H | 3-CH₃ | Cl | 3-Cl | H | viscous mass |
| 34 | —CH₃ | H | —O—CF₃ | H | Cl | 3-Cl | H | m.p. 143–145° C. |
| 35 | Cl | H | H | H | H | H | H | m.p. 70–72° C. |
| 36 | Cl | H | H | 3-CH₃ | H | H | H | m.p. 104–106° C. |
| 37 | Cl | H | —O—CF₃ | H | H | H | H | m.p. 133–135° C. |

-continued

| Compound | $R_1$ | $R_2$ | $R_3$ | $R_4$ | $R_5$ | $R_6$ | $R_7$ | Physical data |
|---|---|---|---|---|---|---|---|---|
| 38 | Cl | H | H | H | F | H | H | m.p. 126–128° C. |
| 39 | Cl | H | H | 3-CH$_3$ | F | H | H | m.p. 130–132° C. |
| 40 | Cl | H | —O—CF$_3$ | H | F | H | H | m.p. 141–142° C. |
| 41 | Cl | H | F | H | F | H | H | m.p. 149–152° C. |
| 42 | Cl | H | H | H | H | 2-Cl | 6-Cl | m.p. 144–146° C. |
| 43 | Cl | H | H | 3-CH$_3$ | H | 2-Cl | 6-Cl | m.p. 174–176° C. |
| 44 | Cl | H | —O—CF$_3$ | H | H | 2-Cl | 6-Cl | m.p. 192–193° C. |
| 45 | H | 2-Cl | H | H | Cl | H | H | viscous mass |
| 46 | H | 2-Cl | H | 3-CH$_3$ | Cl | H | H | m.p. 182–184° C. |
| 47 | H | 2-Cl | —O—CF$_3$ | H | Cl | H | H | viscous mass |
| 48 | H | 2-Cl | F | H | Cl | H | H | viscous mass |
| 49 | H | 2-Cl | H | H | —CH$_3$ | H | H | m.p. 141–143° C. |
| 50 | H | 2-Cl | —O—CF$_3$ | H | —CH$_3$ | H | H | $n_{20}^D = 1.5695$ |
| 51 | F | H | Cl | H | F | H | H | m.p. 140–142° C. |
| 52 | F | H | F | H | F | H | H | m.p. 127–130° C. |
| 53 | Cl | H | —O—CF$_3$ | H | Cl | H | H | m.p. 139–140° C. |
| 54 | Cl | H | Cl | H | Cl | H | H | m.p. 64–68° C. |
| 55 | Cl | H | F | H | Cl | H | H | m.p. 156–158° C. |
| 56 | F | H | —O—CF$_3$ | H | H | H | H | m.p. 106–107° C. |
| 57 | F | H | F | H | H | H | H | m.p. 111–112° C. |
| 58 | F | H | Cl | H | H | H | H | viscous mass |
| 59 | F | H | H | H | Cl | H | H | m.p. 123–125° C. |
| 60 | F | H | H | 3-CH$_3$ | Cl | H | H | m.p. 130–134° C. |
| 61 | F | H | —O—CF$_3$ | H | Cl | H | H | m.p. 148–150° C. |
| 62 | F | H | H | 3-CF$_3$ | Cl | H | H | viscous mass |
| 63 | F | H | Cl | H | Cl | H | H | m.p. 110–112° C. |
| 64 | F | H | F | H | Cl | H | H | m.p. 125–127° C. |
| 65 | Cl | H | —CO—O—CH(CH$_3$)$_2$ | H | Cl | H | H | m.p. 86–88° C. |
| 66 | Cl | H | —OCF$_2$CHF$_2$ | H | Cl | H | H | m.p. 124–126° C. |
| 67 | F | H | —OCF$_2$CHF$_2$ | H | F | H | H | m.p. 134–136° C. |
| 68 | F | H | —CO—O—CH(CH$_3$)$_2$ | H | F | H | H | m.p. 65–68° C. |
| 69 | Cl | H | —CO—O—CH(CH$_3$)$_2$ | H | F | H | H | m.p. 74–76° C. |
| 70 | Cl | H | —OCF$_2$CHF$_2$ | H | F | H | H | m.p. 160–162° C. |
| 71 | F | H | —CO—O—CH(CH$_3$)$_2$ | H | Cl | H | H | m.p. 70–72° C. |
| 72 | F | H | —OCF$_2$CHF$_2$ | H | Cl | H | H | m.p. 145–147° C. |
| 73 | F | H | H | 3-CF$_3$ | F | H | H | m.p. 110–112° C. |
| 74 | F | H | —O—CH$_3$ | H | F | H | H | m.p. 106–111° C. |
| 75 | F | H | —CH$_3$ | H | F | H | H | m.p. 146–148° C. |
| 76 | F | H | H | 3-Cl | F | H | H | m.p. 138–140° C. |
| 77 | F | H | —CF$_3$ | H | F | H | H | m.p. 189–191° C. |
| 78 | H | H | —CO—O—CH(CH$_3$)$_2$ | H | 3,4—O—CH$_2$—O— | | H | viscous mass |
| 79 | —O—CHF$_2$ | H | —O—CF$_3$ | H | F | H | H | m.p. 99–100° C. |
| 80 | —O—CHF$_2$ | H | F | H | F | H | H | m.p. 147–148° C. |
| 81 | —O—CHF$_2$ | H | Cl | H | F | H | H | m.p. 134–136° C. |
| 82 | —O—CHF$_2$ | H | H | H | F | H | H | m.p. 109–111° C. |
| 83 | F | H | Cl | 3-Cl | F | H | H | m.p. 195–196° C. |
| 84 | F | H | H | 3-F | F | H | H | m.p. 121–122° C. |
| 85 | F | H | H | 2-CF$_3$ | F | H | H | m.p. 107–108° C. |
| 86 | F | H | Br | H | F | H | H | m.p. 152–154° C. |
| 87 | F | H | H | 2-F | F | H | H | m.p. 140–142° C. |

The following compounds of formula I can also be obtained in accordance with the procedures described above:

| Compound | $R_1$ | $R_2$ | $R_3$ | $R_4$ | $R_5$ | $R_6$ | $R_7$ |
|---|---|---|---|---|---|---|---|
| 88 | Cl | H | Cl | H | F | H | H |
| 89 | F | H | Cl | H | —CF$_3$ | H | H |
| 90 | F | H | —O—CF$_3$ | H | —CF$_3$ | H | H |
| 91 | F | H | —CO—O—CH(CH$_3$)$_2$ | H | —CF$_3$ | H | H |
| 92 | —O—CHF$_2$ | H | Cl | H | Cl | H | H |
| 93 | —O—CHF$_2$ | H | Cl | H | CF$_3$ | H | H |
| 94 | —O—CHF$_2$ | H | —O—CF$_3$ | H | Cl | H | H |
| 95 | —O—CHF$_2$ | H | —O—CF$_3$ | H | CF$_3$ | H | H |
| 96 | —O—CHF$_2$ | H | —CO—O—CH(CH$_3$)$_2$ | H | F | H | H |
| 97 | —O—CHF$_2$ | H | —CO—O—CH(CH$_3$)$_2$ | H | Cl | H | H |
| 98 | —O—CHF$_2$ | H | —CO—O—CH(CH$_3$)$_2$ | H | CF$_3$ | H | H |

EXAMPLE 2

Formulations for liquid active ingredients of formula I according to Example 1 or combinations thereof with other insecticides or acaricides (throughout, percentages are by weight)

| 1. Emulsifiable concentrates | (a) | (b) | (c) |
|---|---|---|---|
| active ingredient or active ingredient combination | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexane | — | 15% | 20% |
| xylene mixture | 65% | 25% | 20% |

Emulsions of any required concentration can be produced from such concentrates by dilution with water.

| 2. Solutions | (a) | (b) | (c) | (d) |
|---|---|---|---|---|
| active ingredient or active ingredient combination | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| expoxidised coconut oil | — | — | 1% | 5% |
| ligroin (boiling range 160–190°) | — | — | 94% | — |

These solutions are suitable for application in the form of microdrops.

| 3. Granulates | (a) | (b) |
|---|---|---|
| active ingredient or active ingredient combination | 5% | 10% |
| kaolin | 94% | — |
| highly dispersed silicic acid | 1% | — |
| attapulgite | — | 90% |

The active ingredient or active ingredient combination is dissolved in methylene chloride, the solution is sprayed onto the carrier, and the solvent is subsequently evaporated off in vacuo.

| 4. Dusts | (a) | (b) |
|---|---|---|
| active ingredient or active ingredient combination | 2% | 5% |
| highly dispersed silicic acid | 1% | 5% |
| talcum | 97% | — |
| kaolin | — | 90% |

Ready for use dusts are obtained by intimately mixing the carriers with the active ingredient or active ingredient combination.

Formulations for solid active ingredients of formula I according to Example 1 or combinations thereof with other insecticides or acaricides (throughout, percentages are by weight)

| 1. Wettable powders | (a) | (b) | (c) |
|---|---|---|---|
| active ingredient or active ingredient combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or active ingredient combination is thoroughly mixed with the adjuvants and the mixture is thoroughly ground in a suitable mill, affording wettable powders which can be diluted with water to give suspensions of any desired concentration.

| 2. Emulsifiable concentrate | |
|---|---|
| active ingredient or active ingredient combination | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | (a) | (b) |
|---|---|---|
| active ingredient or active ingredient combination | 5% | 8% |
| talcum | 95% | — |
| kaolin | — | 92% |

Ready for use dusts are obtained by mixing the active ingredient or active ingredient combination with the carrier, and grinding the mixture in a suitable mill.

| 4. Extruder granulate | |
|---|---|
| active ingredient or active ingredient combination | 10% |
| sodium lignosulfonate | 2% |
| carboxymethylcellulose | 1% |
| kaolin | 87% |

The active ingredient or active ingredient combination is mixed and ground with the adjuvants, and the mixture is subsequently moistened with water. The mixture is extruded, granulated and then dried in a stream of air.

| 5. Coated granulate | |
|---|---|
| active ingredient or active ingredient combination | 3% |
| polyethylene glycol 200 | 3% |
| kaolin | 94% |

The finely ground active ingredient or active ingredient combination is uniformly applied, in a mixer, to the kaolin moistened with polyethylene glycol. Non-dusty coated granulates are obtained in this manner.

| 6. Suspension concentrate | |
|---|---|
| active ingredient or active ingredient combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |

-continued

| 6. Suspension concentrate | |
|---|---|
| 37% aqueous formaldehyde solution | 0.2% |
| silicone oil in the form of a 75% aqueous emulsion | 0.8% |
| water | 32% |

The finely ground active ingredient or active ingredient combination is intimately mixed with the adjuvants, giving a suspension concentrate from which suspensions of any desired concentration can be obtained by dilution with water.

EXAMPLE 3: Action against *Musca domestica*

50 g of freshly prepared nutrient substrate for maggots are charged into each of a number of beakers. A specific amount of an acetonic solution containing 1% by weight of the respective test compound is pipetted onto the nutrient substrate present in the beakers to give an acitve ingredient concentration of 800 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient at the given concentration. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

The compounds of formula I according to Example 1 exhibit good activity in this test.

EXAMPLE 4: Action against *Aedes aegypti*

A concentration of 800 ppm is obtained by pipetting a specific amount of an acetonic solution containing 0.1% by weight of the test compound onto the surface of 150 ml of water in a beaker. After the acetone has evaporated, 30 to 40 two-day-old larvae of *Aedes aegypti* are put into the beaker containing the test compound. Mortality counts are made after 1, 2 and 5 days.

In this test, the compounds of formula I according to Example 1 exhibit good activity against *Aedes aegypti*.

EXAMPLE 5: Insecticidal stomach poison action

Cotton plants about 25 cm high, in pots, are sprayed with aqueous emulsions containing the respective test compound in concentrations of 100, 200 and 400 ppm. After the spray coating has dried, the cotton plants are populated with *Spodoptera littoralis* and *Heliothis virescens* larvae in the $L_3$-stage. The test is carried out at 24° C. and 60% relative humidity. The percentage mortality of the test insects is determined after 120 hours.

In this test, the compounds of the present invention effect 80 to 100% mortality at the following concentrations:

| Compound | Active ingredient concentration | |
|---|---|---|
| | Spodoptera | Heliothis |
| 13 | 400 ppm | — |
| 15 | 400 ppm | 400 ppm |
| 31 | 400 ppm | — |
| 37 | 400 ppm | 400 ppm |
| 40 | 400 ppm | 200 ppm |
| 51 | — | 100 ppm |
| 54 | — | 400 ppm |
| 56 | 400 ppm | 400 ppm |

EXAMPLE 6: Action against *Anthonomus grandis* (Adults)

Cotton plants in pots are sprayed with a wettable aqueous emulsion formulation containing 400 ppm of the test compound. After the spray coating has dried (about 1½ hours), each plant is populated with 10 adult unsexed beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation of the stomach poison action is made after 1, 2, 3 and 6 days on the basis of the percentage mortality of the beetles (percentage in dorsal position).

The surviving beetles are transferred to Anthonomus diat pellets and left for 3 days for oviposition. The beetles are then removed and the pellets with the egg deposits are incubated for 7 days at 28° C. Evaluation of the reproduction inhibiting effect is made by determining the reduction in the number of deposited eggs, the number of larvae which have hatched from these eggs and the number of dead larvae in comparison with untreated controls.

At a concentration of 400 ppm, with respect to stomach poison action, compounds 1, 4, 13 and 15 and, with respect to reproduction inhibition, compounds 7, 8 18, 19, 20 and 22 according to Example 1 effect 80 to 100% mortality in comparison with untreated controls.

Example 7: Action against soil insects (*Diabrotica balteata*)

5 maize seedlings 1 to 3 cm in height and a filter paper disc are immersed in an aqueous solution of the test compound containing about 4% by volume of acetone. The immersed filter paper disc is placed on the bottom of a plastic beaker (contents 200 ml) and on it is then placed a dry filter paper disc together with the maize seedlings and 10 larvae of *Diabrotica balteata* in the $L_2$ or $L_3$ stage. The batch is kept at about 24° C. and 40 to 60% relative humidity under daylight. Evaluation is made after 6 days in comparison with untreated controls.

At the following concentrations, the compounds of the present invention effect 80 to 100% mortality:

| Compound | Active ingredient concentration |
|---|---|
| 1 and 53 | 3 ppm |
| 11, 15 and 40 | 12.5 ppm |
| 7, 51, 56 and 61 | 50 ppm |
| 4, 37, 54 and 63 | 100 ppm |
| 58 | 200 ppm |
| 1 and 6 | 400 ppm |

EXAMPLE 8: Action against *Laodelphax striatellus* and *Nilaparvata lugens* (nymphs)

The test is carried out with growing plants. For this purpose 4 rice plants (thickness of stem 8 mm) about 20 cm in height are planted into each of a number of pots (diameter 8 cm). The plants in each pot are sprayed on a rotary table with 100 ml of an acetonic solution containing 400 ppm of the test compound. After the spray coating has dried, each plant is populated with 20 nymphs of the test organisms in the third stage. To prevent the cicadas from escaping, a glass cylinder is slipped over each of the plants and sealed with a gauze top. The nymphs are kept for 10 days on the treated plant until the next development stage has been reached. Evaluation of percentage mortality is made 1, 4 and 8 days after treatment.

The compounds of formula I according to Example 1 of the present invention exhibit good activity in this test.

Example 9: Action against *Laodelphax striatellus* and *Nilaparvata lugens* (ovicidal)

The test is carried out with growing plants. For this purpose 4 rice plants (thickness of stem 8 mm; height about 20 cm) are planted into each of a number of pots (diameter 8 cm).

The plants in each pot are sprayed on a rotary table with 100 ml of an acetonic solution containing 400 ppm of the test compound. After the spray coating has dried, each plant is populated with 3 adult females. To prevent the females from escaping, a glass cylinder is slipped over each of the plants and sealed with a gauze top. The females are left on the plant for 4 days for oviposition and are then removed.

About 8 days after the females have been placed on the plants, the young cicadas hatch from the eggs and a count is made. The percentage mortality is calculated by comparing the number of larvae which have hatched on the treated plants with the number which have hatched on the untreated control plants.

The compounds of formula I according to Example 1 exhibit good ovicidal activity in this test.

What is claimed is:

1. A compound of the formula

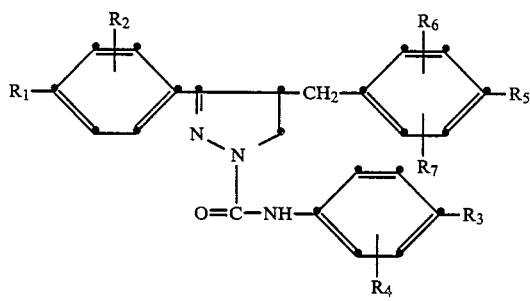

wherein:
$R_1$ is chlorine or fluorine;
$R_3$ is $OCF_3$;
$R_5$ is fluorine or chlorine; and
$R_2$, $R_4$, $R_6$ and $R_7$ are hydrogen.

2. A compound according to claim 1 of the formula

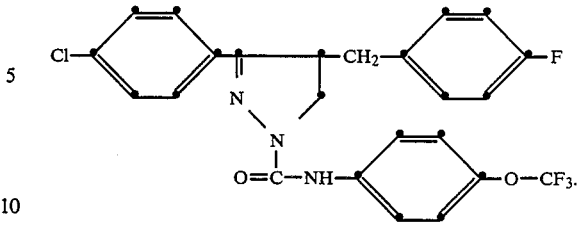

3. A compound according to claim 1 of the formula

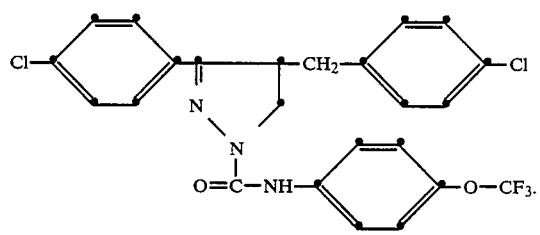

4. A compound according to claim 1 of the formula

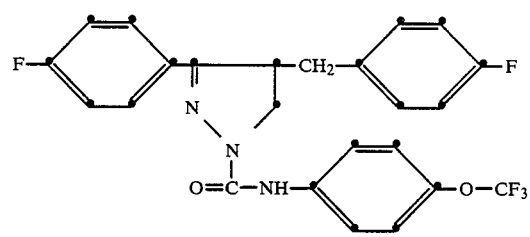

5. A composition for controlling insects and representatives of the order Acarina which contains as active ingredient an amount effective to control insects or members of the order Acarina of at least one compound of the formula

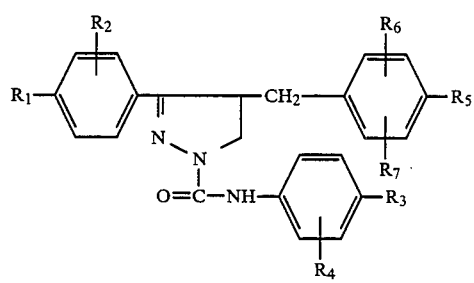

wherein
$R_1$ is chlorine or fluorine;
$R_3$ is $OCF_3$;
$R_5$ is fluorine or chlorine; and
$R_2$, $R_4$, $R_6$ and $R_7$ are hydrogen together with an inert carrier.

6. A method of controlling insects and representative of the order Acarina, which method comprises contacting or treating said insects and representatives of the order Acarina or the locus thereof with an amount effective to control insects or members of the order Acarina of a compound of the formula

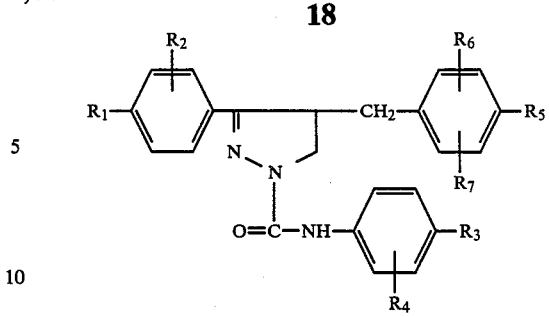
wherein
R₁ is chlorine or fluorine;
R₃ is OCF₃;
R₅ is fluorine or chlorine; and
R₂, R₄, R₆ and R₇ are hydrogen.
7. A method according to claim 6 wherein said insects or representatives of the order Acarina are in their larval stage.
8. A method according to claim 6 wherein said insects or representative of the order Acarina are plant-destructive soil insects.
* * * * *